United States Patent [19]

Meyer et al.

[11] Patent Number: 5,410,096
[45] Date of Patent: Apr. 25, 1995

[54] PLANTS WITH MODIFIED FLOWER COLOR AND METHODS FOR THEIR PRODUCTION BY GENETIC ENGINEERING

[76] Inventors: Peter Meyer, Auf dem Rosenhügel 28, D-5000 Köln 50; Iris Heidmann, Ludwig-Jahn-Str. 54, D-5000 Köln 40; Heinz Saedler, Egelspfad, D-5000 Köln 30; Gert Forkmann, Auf der Morgenstelle 28, D-7400 Tübingen, all of Germany

[21] Appl. No.: 573,876

[22] Filed: Aug. 28, 1990

Related U.S. Application Data

[63] Continuation of Ser. No. 269,491, Nov. 10, 1988, abandoned.

[30] Foreign Application Priority Data

Nov. 13, 1987 [DE] Germany .................. 37 38 657.3

[51] Int. Cl.⁶ .................. A01H 5/00; A01H 1/06; C12N 15/82; C12N 15/53
[52] U.S. Cl. .................. 800/205; 800/DIG. 67; 935/60; 935/67; 435/75; 435/172.1; 435/172.3; 435/240.4; 435/320.1; 435/317.1
[58] Field of Search .................. 800/205; 435/172.3, 435/240.4, 320, 317.1, 320.1; 935/67

[56] References Cited

U.S. PATENT DOCUMENTS 4,771,002 9/1988 Gelvin .................. 435/172.3

OTHER PUBLICATIONS

Sanders et al., 1987, (Feb.), Nucleic Acids Research, 15:1543–1558.
J. B. Harborne's, "Comparative Biochemistry of Flavonoids", (1967), pp. 1–37, 87–91, 184–190.
Hain, et al., Mol. Gen. Genet., vol. 199, (1985), pp. 161–168.
Forkmann, et al., pp. 1146–1148, Z. Naturforsch, (1987).
The Plant Cell, vol. 2, pp. 849–856, Sep. 1990, Befey, et al.
Schwarz–Sommer et al., 1987, EMBO J., 6(2):287–294.
Cornu et al., 1974, Phytochemistry 13:2022.
Forkmann et al., 1987, Z. Naturforsch, 42c:1146–1148.
Wiering et al., 1984, Inheritance and Biochemistry of Pigments in Petunia Monograph, (Sink ed.), Springer, pp. 49–67.
Rothstein et al., 1987, Gene, 53:153–161.
H. Schneiders, et al., New Flower Colours via Gene Transfer, Abstracts VIIth International Congress on Plant Tissue and Cell Culture, 1990, p. 180.

Primary Examiner—Elizabeth C. Weimar
Assistant Examiner—P. R. Rhodes
Attorney, Agent, or Firm—John R. Wetherell, Jr.; Spensley Horn Jubas & Lubitz

[57] ABSTRACT

Described are plants not naturally capable of reducing dihydrokaempferol and containing a DNA sequence inserted according to recombinant DNA techniques which DNA sequence encodes a protein with the enzymatic activity of a dihydroflavonol 4-reductase (DFR) with extended substrate specificity for dihydrokaempferol. Furthermore, methods for the production of said plants, recombinant vectors and the use of said plants for the breeding of plants and parts of plants with modified flower colour are described.

6 Claims, 4 Drawing Sheets

PLANTS WITH MODIFIED FLOWER COLOR AND METHODS FOR THEIR PRODUCTION BY GENETIC ENGINEERING

This is a continuation of application Ser. No. 269,491, filed on Nov. 1, 1988, now abandoned.

BACKGROUND OF THE INVENTION

It is pigments synthesized by a plant which produce the flower colour of plants.

As is known, there is a great demand for plants with new flower colours. Hitherto it has been attempted to meet this demand by cross-breeding to produce plants with new flower colours. However, this "classical" plant breeding technique was limited by the boundaries of the genetic compatibility of the various plant species used for cross-breeding.

For example, it was not possible to use these methods to breed brick red petunias (*Petunia hybrida*), because the genetic information for the key enzyme of the synthesis pathway of the corresponding pigment does not occur in petunia species.

This genetic information cannot be cross-bred into *Petunia hybrida* from other plant species in which it is found, e.g. from maize (*Zea mays*) or the snapdragon (*Antirrhinum majus*). *Petunia hybrida* and *Zea mays* or *Antirrhinum majus* are genetically incompatible.

It was also the prevailing opinion in the prior art that even if someone did succeed in inserting genes from monocotyle-donous plants like *Zea mays* into dicotyle-donous plants like Petunia hybrida, the genes would then no longer be active. These difficulties meant that it has so far only been possible to meet the demand for plants with new flower colours on a limited scale.

SUMMARY OF THE INVENTION

The major object of the invention is to provide plants with modified flower colour which contain a DNA sequence which was inserted according to recombinant DNA techniques and which encodes a protein being enzymatically active in the plant and allowing the synthesis of pigments not naturally occurring in the plant.

A further object of the invention is to provide a method for the production of said plants in which recombinant DNA techniques are applied.

Another object of the invention is to provide recombinant DNA molecules which can be used in the method of the invention and which contain a DNA sequence encoding a protein being enzymatically active in the plant and allowing the synthesis of pigments not naturally occurring in the plant.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE INVENTION

In accordance with the present invention the plants with modified flower colour are constructed by inserting into the plant a DNA sequence according to recombinant DNA techniques which encodes a protein with the enzymatic activity of a dihydroflavonol 4-reductase with extended substrate specificity for dihydrokaempferol (hereinafter abbreviated as DFR; often referred to in the literature as DQR).

The expression "protein with the enzymatic activity of a dihydroflavonol 4-reductase with extended substrate specificity for dihydrokaempferol" denotes a protein that corresponds to a naturally occurring enzyme with the stated specificity, but also denotes proteins not naturally occurring that exhibit the stated specificity. Examples are fusion proteins or proteins containing only an enzymatically active part of the naturally occurring protein.

If the newly inserted genetic information is controlled in the cells of the plant by a suitable promotor, it is expressed. At the same time the enzyme DFR is synthesized in the cells.

Figure 4:
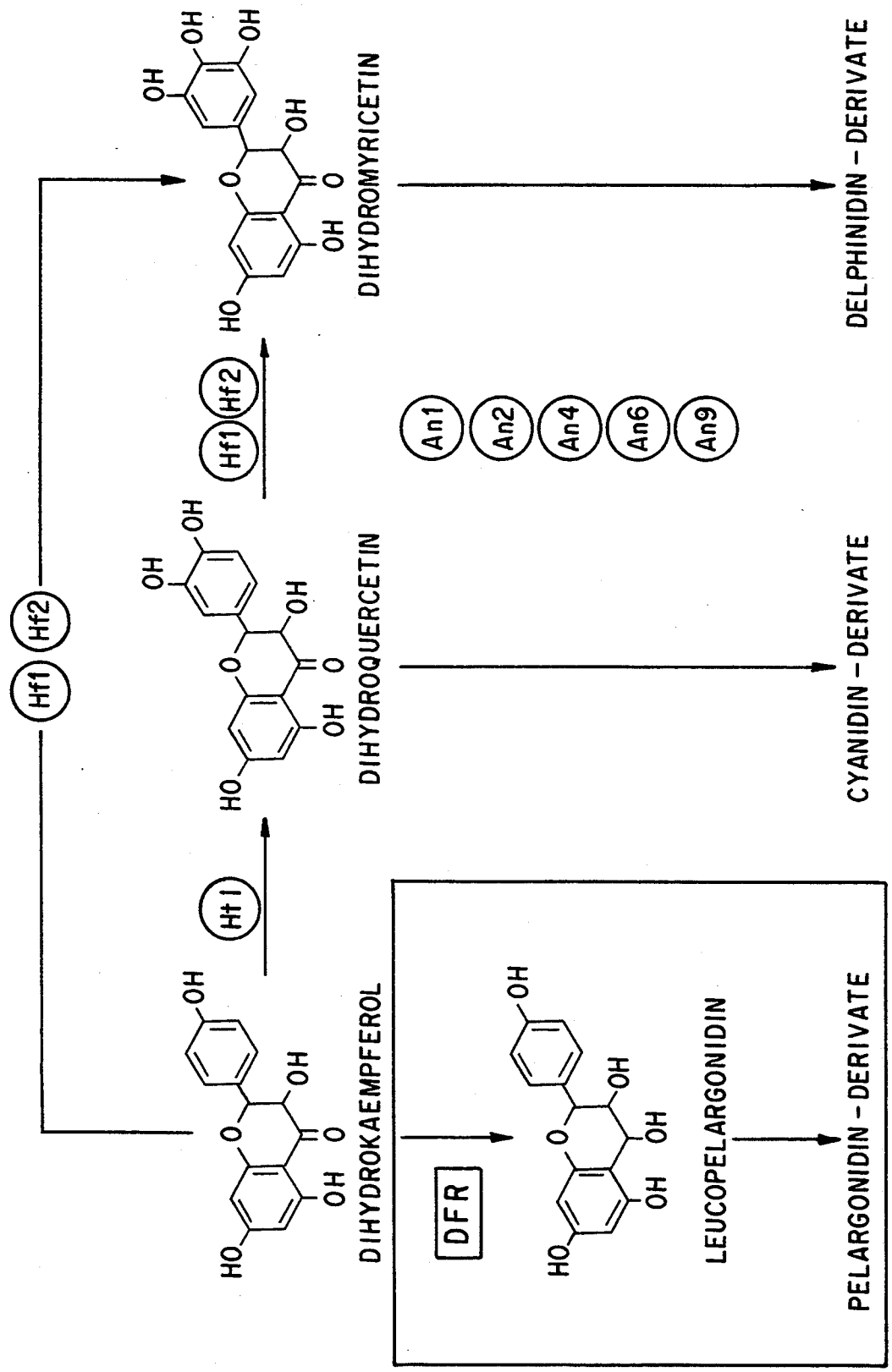
FIG. 4 is a schematic representation of a section of the anthocyanin biosynthesis pathway.

If dihydrokaempferol is produced in the cells as an intermediate of anthocyanin biosynthesis, the synthesized DFR enzyme reduces this to leucopelargonidin (FIG. 4). The other enzymes that are in any case found in the cells modify the leucopelargonidin to brick red anthocyanin pigment pelargonidin 3-glycosides.

The person skilled in the art is familiar with donor plants from which the DFR gene can be isolated. Examples include pelargonidin-producing plants such as *Zea mays*, *Antirrhinum majus*, *Matthiola incana* (stock) and *Callistephus chinensis* (aster).

The skilled person is also familiar with acceptor plants that produce dihydrokaempferol along the anthocyanin biosynthesis pathway, but said dihydrokaempferol cannot be converted into leucopetargonidin for lack of a dihydroflavonol 4-reductase with substrate specificity for dihydrokaempferol. Examples include *Petunia hybrida* and *Nicotiana alata* (tobacco plant).

In a preferred embodiment of the present invention the pelargonidin-producing plants *Zea mays* (monocotyledonous) or *Antirrhinum majus* are used as DFR DNA-donor plants and Petunia hybrida (dicotyledonous) is used as the DQR DNA-acceptor plant.

In *Zea mays* the A1 gene codes for the DFR enzyme. In the aleuron of *Zea mays* said enzyme converts dihydroquercetin into leucocyanidin and dihydrokaempferol into leucopelargonidin, thereby initiating the formation of cyanidin derivatives and pelargonidin derivatives. This dihydroflavonol 4-reductase from *Zea mays* has an extended substrate specificity for dihydrokaempferol.

In accordance with the present invention the DFR DNA from *Zea mays* can be used to construct variants of Petunia hybrida with a brick red flower colour according to recombinant DNA techniques, because they are able to synthesize the brick red anthocyanin pigment pelargonidin 3-glycoside with the aid of the inserted DFR DNA from Zea mays.

Formerly such variants of Petunia hybrida were unknown. The reason for this was that although the dihydroflavonol 4-reductase usually found in petunias is relatively speaking very efficient at converting dihydromyricetin and less efficient at converting dihydroquercetin, it is unable to convert dihydrokaempferol (FIG. 4). This naturally occurring enzyme in Petunia hybrida therefore lacks substrate specificity for dihydrokaempferol, and hence the anthocyanin pigments naturally found in petunias are exclusively delphinidin derivatives (dark blue) or cyanidin derivatives (purple) (FIG. 4). Glycosides are one example of these derivatives.

In one preferred embodiment of the present invention, a mutant of Petunia hybrida with a genetic deficiency for activity of the 3'- and 3',5'-hydroxylases is used as the acceptor plant (cf. the enzymes designated as Ht1, and Hf1 and Hf2, in FIG. 4).

As a result of this deficiency the plant concerned accumulates dihydrokaempferol and kaempferol, because these compounds are not converted into dihydroquercetin and dihydromyricetin in the course of anthocyanin biosynthesis (FIG. 4). Hence the plant lacks the anthocyanin pigments synthesized on the basis of these intermediates, namely cyanidin derivatives (purple) and delphinidin derivatives (dark blue). Its flower colour is therefore essentially white or pale pink.

The skilled person is familiar with the preparation of such defective mutants. One example, mutant RL01, is described by G. Stotz in Theor. Appl. Genet. 70 (1985), pp. 300–305. This mutant from the Petunia hybrida collection in Tubingen, Fed. Rep. of Germany, is a derivative of line R4 which has previously been used for genetic and enzymatic studies on B-ring hydroxylation and flavonol formation. Since the mutant RL01 contains recessive alleles at the Ht1 and Hf1 loci, it lacks flavonoid 3'-hydroxylase activity and exhibits only low flavonoid 3',5'-hydroxylase activity, resulting in the accumulation of only small amounts of cyanidin and delphinidin derivatives and hence it has a pale pink flower colour. Anthocyanins based on pelargonidin are not synthesized by this mutant. Instead, due to the genetic defects mentioned above and due to the inability to convert dihydrokaempferol to leucopelargonidin, dihydrokaempferol is accumulated (FIG. 4). If the anthocyanin synthesis intermediate leucopelargonidin is supplemented to the mutant RL01 in the usual manner it is converted to pelargonidin 3-glycoside and brick red flower petals are produced (FIG. 4). It therefore follows that all other genes necessary for anthocyanin biosynthesis are represented by dominant alleles. The mutant RL01 is thus apparently only defective in the enzymes responsible for the hydroxylation of dihydrokaempferol.

Figure 2A:
FIG. 2(A) shows transformant RP235-15 which carries the A1 gene from *Zea mays* in cDNA form. This gene enables the synthesis of pelargonidin 3-glycoside and alters the flower color of mutant RL01.
Figure 2B:
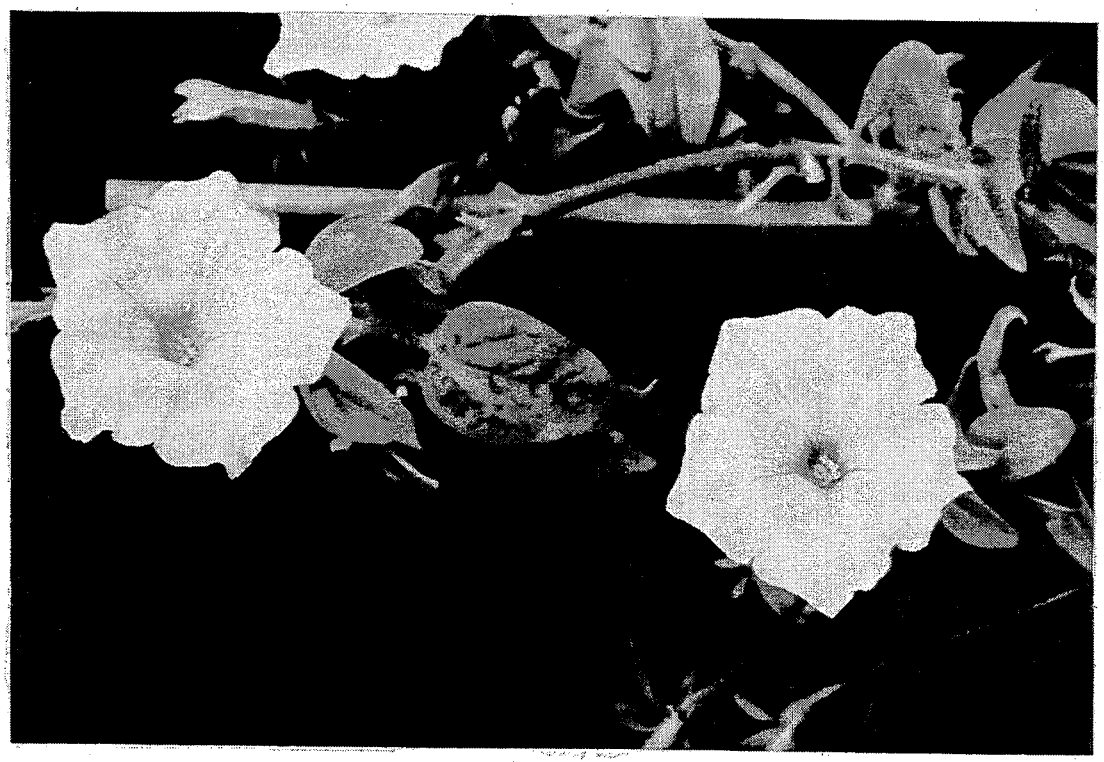
FIG. 2(B) shows untransformed mutant RL01 which has a pale pink flower color due to traces of cyanidin and delphinidin derivatives.

If in accordance with the invention the DFR gene is inserted into the foregoing Petunia hybrida mutants, for example into RL01, the flower colour is then modified to a brick red which commonly exhibits the flower characteristics typical of Petunia hybrida (FIG. 2).

The genetically engineered insertion of the DNA sequence coding for the DFR can be performed using conventional techniques, for example by microinjection (A. de la Pena, H. Lorz & J. Schell, Nature 325 (1987), pp. 274–276), electroporation (M. E. Fromm, L. P. Taylor & V. Walbot, Nature 319 (1986), pp. 791–793), transformation (F. A. Krens, L. Molendijk, G. J. Wullems, R. A. Schilperoort, Nature 296 (1982), pp. 72–74), transfer of corresponding Ti plasmids (L. Marton, G. J. Wullems, L. Molendijk, R. A. Schilperoort, Nature 277 (1979), pp. 129–131), and by liposome-mediated transfer (R. T. Fraley, Plant Mol. Biology 2, p. 5 et seqq.). Conventional vectors, for example the Ti plasmid, are suitable for introducing the DNA.

Such vector systems are explained in L. Herrera Estrella et al., Nature 303 (1983), 209; L. Herrera Estrella et al., EMBO J. 2 (1983), 987; J. P. Hernalsteens et al., Nature 287 (1980), 654 and in R. T. Fraley et al., Proc. Natl. Acad. Sci. USA 80 (1983), 4803.

In addition the Ti plasmid system is described in, for example, EP-A1-0 116 718.

The DNA sequence is preferably inserted into protoplasts of the acceptor plant which had been synchronized and are in the M-phase of the cell cycle. This transformation technique is described by P. Meyer et al. in Mol. Gen. Genet. 201 (1985), pp. 513–528.

Depending on the vector system used, it is also possible to insert the DNA sequence along with protoplasts into cells and tissue of the plant.

Recombinant vector p35A1 is preferably used. Under the control of the CaMV (Cauliflower Mosaic Virus) 35S promotor contained in this vector, the Zea mays A1 gene cloned as cDNA is expressed constitutively. In addition, apart from the DFR gene a kanamycin resistance gene is simultaneously transferred with this vector to the plant, with the result that plants transformed with the vector can readily be selected on the basis of their resistance to kanamycin.

The invention is illustrated by the following examples.

Further information about DNA recombination techniques can be found in Maniatis et al., "Molecular Cloning", CSH Laboratory, Cold Spring Harbor, N.Y. (1982).

Example 1:

Construction of the p35A1 Vector

The isolation of a cDNA sequence of the A1 gene, and in particular that of the type 2 A1 gene, is described by Z. Schwarz-Sommer et al. in EMBO J. 2 (1987), pp. 287–294.

First, in a 1320bp EcoRI fragment of a full-size cDNA clone of a type 2 A1 gene of Zea mays the EcoRI restriction sites are filled in and XbaI-linkers are attached which restore the infilled EcoRI sites. The resulting XbaI fragment is cloned into the unique XbaI restriction site of plasmid pCKan1, where it is located between the 35S promoter and the terminator sequence of CaMV (Cauliflower Mosaic Virus). The larger EcoRI fragment of plasmid pCKan1 derives originally from plasmid pLGV11, which carries a gene for kanamycin resistance. This allows selection of the plant cells transformed with plasmid pCKan1 on the basis of their kanamycin resistance. Plasmid pLGV11 is equivalent to plasmid pLGV1103, except for the deleted Tn903 SalI fragment (R. Hain et al., Mol. Dev. Denet. 199 (1985), pp. 161–181.

Figure 1:
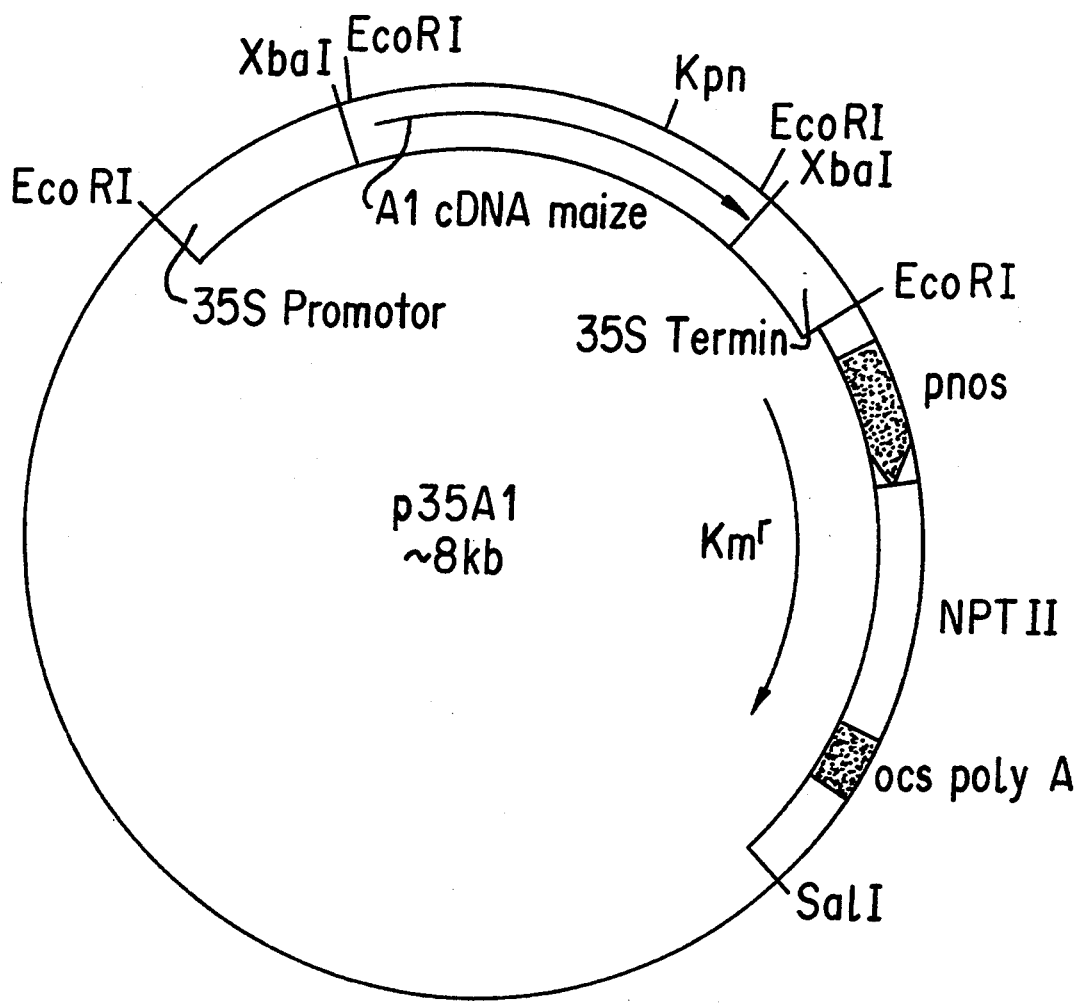
FIG. 1 is a restriction map of vector p35A1.

The plasmid obtained in this construction is plasmid p35A1 (FIG. 1). This was deposited at the Deutsche Sammlung von Mikroorganismen (German Culture Collection) on Oct. 14, 1987 under the accession number DSM 4275.

Example 2:

Construction of a *Petunia hybrida* with brick red flower colour

Protoplasts of Petunia hybrida RL01 mutant synchronized into M-phase are transformed with plasmid p35A1 from Example 1 as described by Meyer et al., loc. cit..

After transformation microcalli are cultured and selected in bead-type culture in V47-medium reducing osmolarity to 100 mosm per week (R. D. Shilito et al., Plant Cell Rep. 2 (1983), pp. 244–247; H. Binding, Z. Pflanzenphysiol. 74 (1974), pp. 327–356). Kanamycin-resistant microcalli are transferred to regeneration medium when they reach a diameter 3–5 mm. They are placed for three weeks on Re27/6-medium (MS-medium with 2 mg/l BAP (benzylaminopurin) and 2 mg/l IAA (indole acetic acid); T. Murashige, Physiol. Plant. 15 (1962), pp. 473–497) and are then transferred to Re17/3-medium (MS-medium with 1 mg/l BAP and 1 mg/l IAA). The shoots are rooted on MS-medium without hormones. All media contain 50 mg/l kanamycin.

Two percent of the surviving calli express the gene for kanamycin resistance encoded by plasmid p35A1 and are therefore resistant to kanamycin. From each transformed callus two plants are regenerated.

Figure 3:
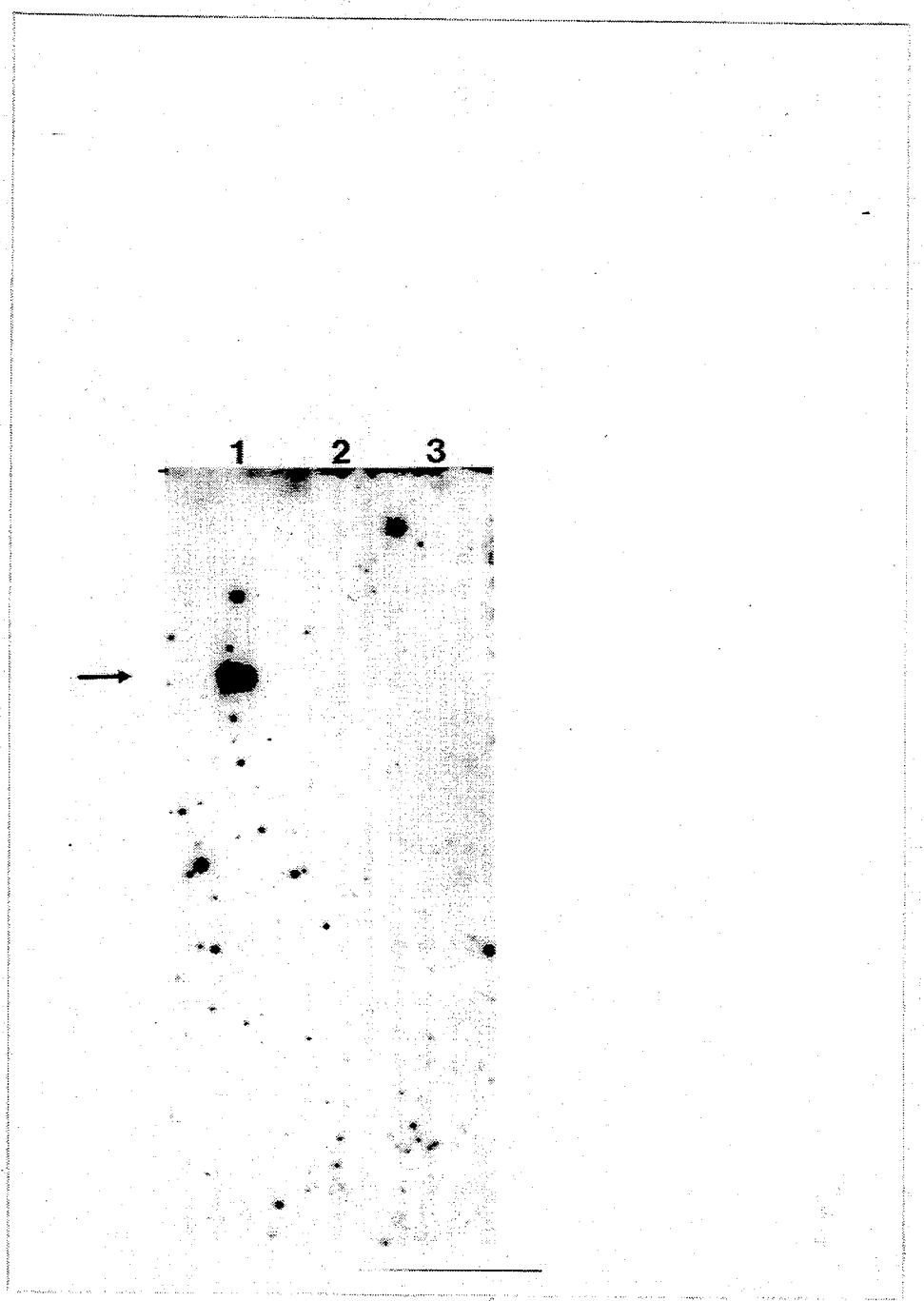
FIG. 3 shows a Northern Blot in which the transcription of the A1 gene from *Zea mays* in transgenic *Petunia hybrida* plants was determined. Transformant RP235-15 shows strong mRNA expression of the *Zea mays* A1 gene (lane 1), while no transcripts of the A1 gene are detectable in transformant RP235-12 with an unchanged flower colour (lane 2). Nor does the untransformed mutant RL01 (the control) exhibit any transcripts of the A1 gene (lane 3).

Of the first 15 flowering transformants two transformed plants show a brick red coloration on the flowers of both regenerated plants (FIG. 2). The appearance of pelargonidin pigment responsible for this brick red flower colour correlates with the transcription of the A1 cDNA from *Zea mays*. This was transferred with plasmid p35A1, in which it is under the control of the CaMV 35S promotor. The transcription is shown by mRNA extraction from the leaves as described by J. Logemann (Analytical Biochemistry 163 (1987), pp. 16–20). Hybond ®-mAP (Amersham) is used according to the manufacturer's instructions. The A1 mRNA isolated from the leaves is visualized in a Northern Blot by hybridization with an EcoRI-XbaI restriction fragment of the A1 cDNA as the probe molecule (A. P. Feinberg et al., Anal. Biochem. 132 (1983), pp. 6–13, and 137 (1983), pp. 266–267) (FIG. 3).

The transformant RP235-15, all the flowers of which are uniformly brick red in colour and in which transcription of the A1 gene was clearly detectable, is used for flavonoid analysis and compared to the mutant RL01. Standard procedures are used (J. B. Harborne, "Comparative Biochemistry of the Flavonoids" Academic Press London and New York (1967)). Small amounts of cyanidin 3-glycoside, cyanidin 3-glycosylglycoside and delphinidin 3-glycoside are contained both in the mutant RL01 and in the transformant RP235-15. However, only the transformant RP235-15 additionally contains pelargonidin 3-glycoside and pelargonidin 3-glycosylglycoside as major components. In the transformant RP235-15 the spectrophotometric peak of anthocyanin has shifted from 528 nm in the mutant RL01 to 512 nm in the transformant RP235-15.

Furthermore, no dihydrokaempferol and only traces of kaempferol are detectable in the transformant RP235-15. As already explained above, these substances are accumulated in the mutant RL01.

This analysis shows that with the help of the expression product of the *Zea mays* A1 gene introduced into the transformant RP235-15 a biosynthesis pathway new to Petunia hybrida has been created. Remarkably, this new pathway has been created in the dicotyledonous plant Petunia hybrida with the help of the cDNA of a gene from the monocotyledonous plant *Zea mays*.

Furthermore, the A1 gene introduced with the vector p35A1 is an easily recognizable marker of the mutant RL01. When this marker is present the flower colour changes from pale pink to brick red. At the level of the phenotype it can thus be discerned with the naked eye whether the transformation with the vector p35A1 has been successful.

We claim:

1. A transgenic plant derived from a plant normally not capable of reducing dihydrokaempferol, where the transgenic plant is comprised of a chimeric DNA construct comprising in the 5' to 3' direction a heterologous promoter which is operably joined to a DNA sequence encoding dihydroflavanol 4-reductase which is operably joined to a transcription termination regulatory region such that the plant tissues containing the translation product of the DNA sequence are able to reduce dihydrokaempferol.

2. The transgenic plant of claim 1, wherein the reduction product of dihydrokaempferol is involved in the formation of pigment in the petal of the transgenic plant.

3. The transgenic plant of claim 2, which is a member of the genus Petunia.

4. The transgenic plant of claim 3, which is a *Petunia hybrida*.

5. The transgenic plant of claim 3, which has a genetic defect at the recessive alleles at loci Ht1, Hf1, and Hf2.

6. The transgenic plant of any one of claims 1, 2, 3, 4, or 5 wherein the chimeric DNA construct is the DNA segment beginning at the EcoRI restriction site 5' to the 35S promoter and ending at the SalI restriction site of the plasmid with accession number DSM 4275.

* * * * *